United States Patent [19]
Wada et al.

[11] 4,306,778
[45] Dec. 22, 1981

[54] EYE REFRACTMETERS USING INFRARED RAYS

[75] Inventors: Shinji Wada; Ikuo Kitao; Yasuo Kato; Taketoshi Ishihara; Yuji Sugahara, all of Tokyo, Japan

[73] Assignee: Tokyo Kogaku Kikai Kabushiki Kaisha, Tokyo, Japan

[21] Appl. No.: 92,978

[22] Filed: Nov. 9, 1979

[30] Foreign Application Priority Data

Nov. 13, 1978 [JP] Japan ................................. 53-139530

[51] Int. Cl.$^3$ .............................................. A61B 3/10
[52] U.S. Cl. ........................................ 351/13; 351/14
[58] Field of Search ............... 351/6, 13, 14; 250/216, 250/206

[56] References Cited

U.S. PATENT DOCUMENTS 3,871,772  3/1975  Munnerlyn et al. ................. 351/13
4,021,102  5/1977  Iizuka .................................... 351/13

Primary Examiner—John K. Corbin
Assistant Examiner—Rodney B. Bovernick
Attorney, Agent, or Firm—Stevens, Davis, Miller & Mosher

[57] ABSTRACT

Eye refractmeter using infrared rays in which the target projecting optical system includes an aperture disc having a semicircular apertures disposed within a circle corresponding to the pupil of the patient's eye with chord portions thereof opposed to each other with a spacing therebetween. The observing optical system includes a disc having a slot located at a position corresponding to the space between the apertures. The apertures and the slots are located in conjugate with the patient's pupil with respect to the objective lens.

4 Claims, 10 Drawing Figures

FIG. I

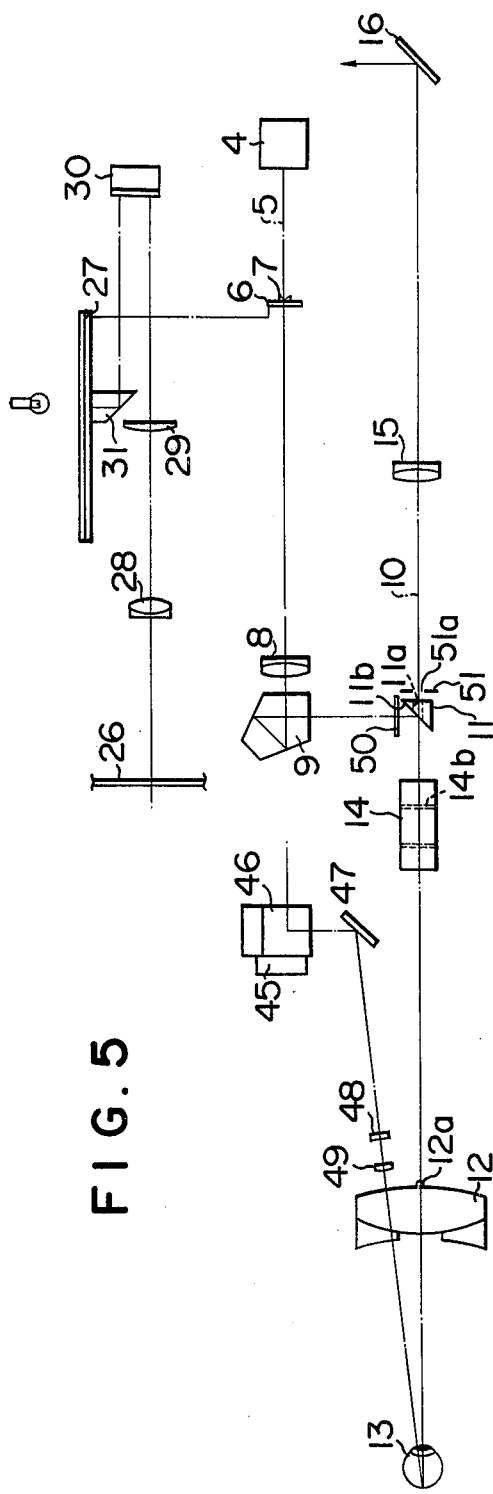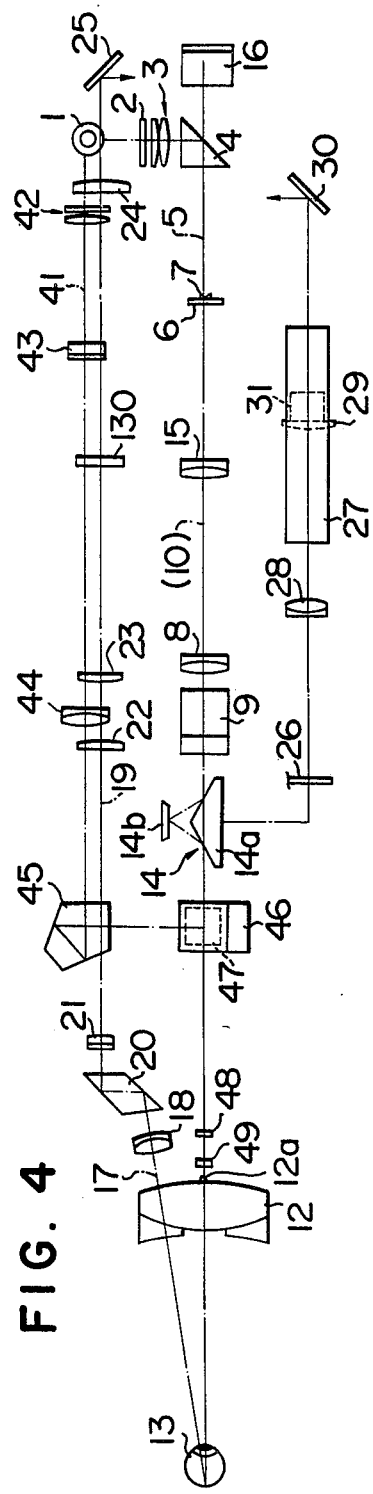
FIG. 5
FIG. 4

EYE REFRACTMETERS USING INFRARED RAYS

The present invention relates to eye refractmeters for determining refractive powers or correcting dioptral values of patient's eyes through observations of target images projected through pupils on retinae of the patient's eyes.

This type of refractmeters generally include a projecting optical system for projecting a target image through the pupil of the patient's eye, and an observing optical system for observing the target image on the retina of the eye. Means is provided for moving the target along the optical axis of the projecting system so that a clear image of the target is obtained on the retina. The position of the target is therefore considered a representing the refractive power of the patient's eye which is then measured in terms of the correcting dioptral value in accordance with the position of the target. For the purpose of observation, there is therefore provided a scale projecting system which projects an indication of the target position in terms of the correcting dioptral value. Means is further provided in order to make it possible to determine the astigmatic axis for rotating the target image about the optical axis of the projecting system. The angle of rotation of the target image is also projected by the scale projecting system for visual observation.

For the observation by the refractmeter, it is required to maintain a predetermined distance and axial alignment between the objective lens of the refractmeter and the patient's eye. For the purpose, the refractmeter is provided with a sighting optical system for observing the light reflected at the anterior segment of the eye.

In such refractmeters, when the target projection is carried out by means of a visual ray, the patient's eye may be dazzled and there may be influences on the results of measurements. Therefore, it is desirable to use an infrared ray for the purpose of the target projection. However, in order to use such infrared ray in the target projection, the observing and sighting optical systems must be provided with noctovision means including image pick-up tubes. Problems encountered in such refractmeters using infrared rays are that the infrared ray is diffused at the retina of the patient's eye making the target image indistinct and that the image forming power of the noctovision means is not so high. As the results, the target image produced by the noctovision means becomes so vague that it cannot be practically used.

Thus, it is required in a refractmeter using infrared ray to provide a split image type focusing system. For this purpose, it is necessary to project two or more separate light bundles through the pupil of the patient's eye. Moreover, it is further necessary to provide an observing aperture which is not superposed with anyone of the projected light. Thus, the optical system is of a very small F-number so that the target image on the noctovision means becomes very obscure. Further, a refractmeter using infrared rays is required to have an increased number of reflective surfaces so that there is a further loss of light.

In an endeavour to solve the problems, the intensity of light may be increased. However, there is an apparent limit in the way of solution because where the infrared ray is too strong there may be a danger of the patient's eye being damaged by heat of the light. As an alternative way, ion multiplying tubes may be used for amplifying the output signals from the image pick-up tubes. However, this will cause a substantial increase in the cost of the refractmeter.

It is therefore an object of the present invention to eliminate the aforementioned problems of an eye refractmeter in which the target projection is carried out by an infrared ray.

Another object of the present invention is to provide an eye refractmeter in which clarity of the target image can be significantly improved.

According to the present invention, the above and other objects can be accomplished by an eye refractmeter comprising a target projecting optical system including objective lens means for projecting an image of target means through a pupil of a patient's eye to produce a target image on retina of the eye, an observing optical system for observing the target image through the pupil and the objective lens means, and a sighting optical system for observing light reflected at anterior segment of the eye to determine that the objective lens means is appropriately apart from the patient's eye, means being provided in said projecting optical system so that the image of the target means is projected by an infrared ray, said target projecting optical system including means for directing at least two target projecting light bundles through said pupil in different angles, said target projecting optical system further including aperture means located substantially in conjugate with the pupil with respect to the objective lens means, said aperture means including within a circle corresponding to the pupil a pair of substantially semicircular apertures located with their chord portions opposed to each other with a space therebetween, said observing optical system including second aperture means located substantially in conjugate with the pupil with respect to the objective lens means, said second aperture means including a slot located in a position corresponding to the space between said semicircular apertures.

When a surface reflector type image rotating element is provided in one of the target projecting optical system and the observing optical system, the element may preferably be coated at its reflecting surfaces with multiple layers of materials which increase light reflecting rate at the surfaces. In an arrangement where the target projecting optical system and the observing optical system have a common optical path through the objecting lens means, such image rotating-element is usually located in the common path. The effect of the multiple layers will be doubled in such an arrangement. The multiple layers may be comprised of alternate layers of $ZrO_2$, $SiO_2$ and $TiO_2$.

The above and other objects and features of the present invention will become apparent from the following descriptions of a preferred embodiment taking reference to the accompanying drawings, in which;

FIG. 4 is a plan view of the optical system shown in FIG. 1;

FIG. 5 is a side view of the optical system shown in FIG. 1;

Figure 1:
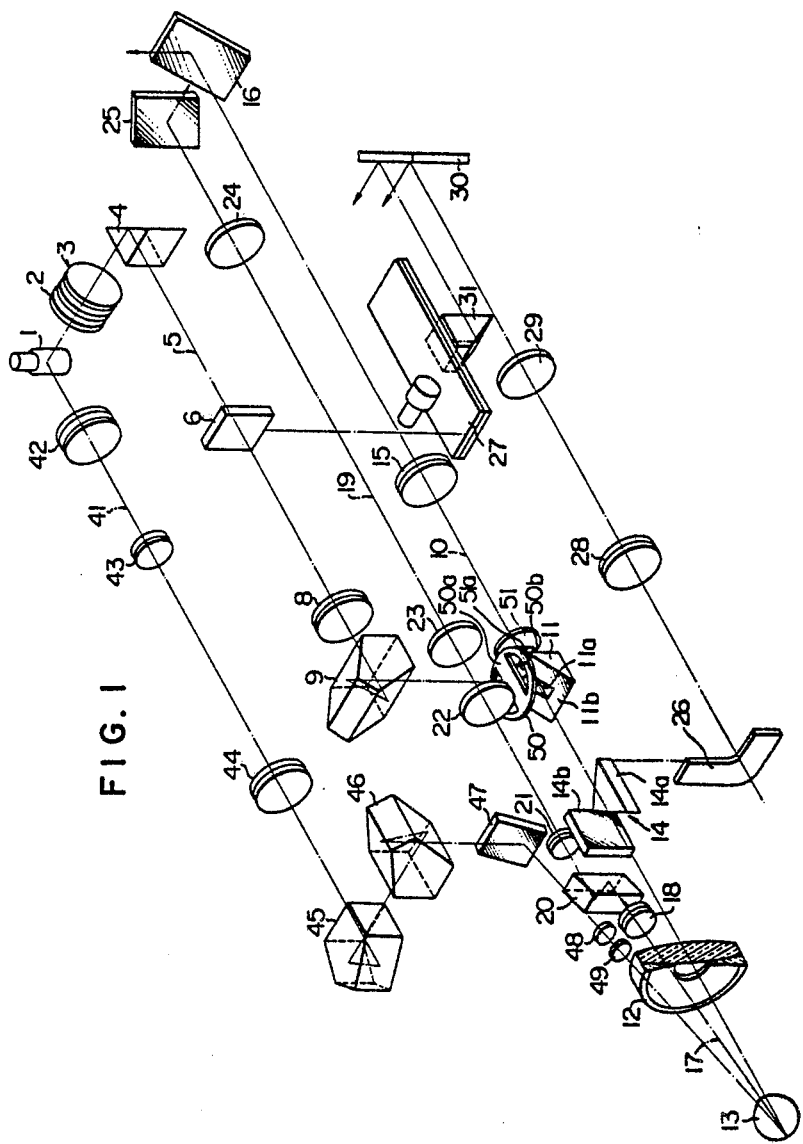
FIG. 1 is a perspective view showing the optical system of an eye refractmeter in accordance with one embodiment of the present invention.

Referring now to the drawings, particularly to FIGS. 1 through 5, the refractmeter shown therein includes a target projecting optical system comprising a light source 1 from which light is passed through a filter 2 which is transparent to infrared ray and then through a collimater lens 3. The light is passed from the lens 3 in the form of a parallel light bundle and reflected by a prism 4 along a projecting optical axis 5. On the axis 5, there is disposed a target 6 which has a target pattern such as that shown in FIG. 6. On the target 6, there is provided an image splitting device 7 such as a crossed-wedge shaped prism assembly. Along the projecting optical system there are also provided a lens 8 and a pentagonal prism 9 which functions to reflect the projecting light downwardly.

Beneath the projecting optical axis 5, there is an observing optical axis 10 and the reflecting optical axis from the prism 9 intersects the axis 10. At the intersection of the axes, there is provided an apertured prism 11 having an aperture 11a coaxial with the optical axis 10 and a reflecting surface 11b for reflecting the projecting light bundle forwardly along the optical axis 10. The projecting light which has been reflected by the reflecting surface 11b of the prism 11 is projected through an objective or projecting lens 12 to a patient's eye 13. The projected light is passed through the pupil of the eye 13 and produces an image of the target on the retina of the eye.

Between the apertured prism 11 and the projecting lens 12, there is disposed an image rotating device 14 which is comprised of a triangular prism 14a and a planar reflecting mirror 14b opposing to the apex of the prism 14a. A rotation of the device 14 about the optical axis 10 causes a rotation of the target image projected through the lens 12.

The target image produced on the retina of the patient's eye is observed by the observing optical system which includes a lens 15 and a reflecting mirror 16 disposed along the optical axis 10 behind the apertured prism 11. Thus, the light reflected at the retina of the eye is passed through the objective lens 12, the image rotating device 14 and the aperture 11a of the prism 11 to the lens 15 from which it is further passed to the reflecting mirror 16 which functions to reflect the light upwardly.

The illustrated refractmeter includes a sighting optical system for determining an exact distance and axial alignment between the lens 12 and the patient's eye 13. The sighting optical system includes a lens 18 disposed behind the objective lens 12 along an optical axis 17 which is inclined with respect to the optical axis 10 and directed through the objective lens 12 to the patient's eye 13. There is further provided a prism 20 which functions to direct the light which has passed through the lenses 12 and 18 along an optical axis 19 extending parallely with respect to the optical axis 10. Along the optical axis 19, there are provided a series of lenses 21, 22, 23 and 24 and the light through the lenses is reflected laterally by a reflecting mirror 25.

The scale projecting system includes an angular scale 26 which is interconnected with the image rotating device 14 to rotate therewith and a dioptral scale 27 which is interconnected with the target 7 to move therewith. The angular scale 26 is projected through lenses 28 and 29 and reflected laterally by a mirror 30. The dioptral scale 27 is projected through a prism 31 and reflected laterally by the mirror 30.

Figure 2:
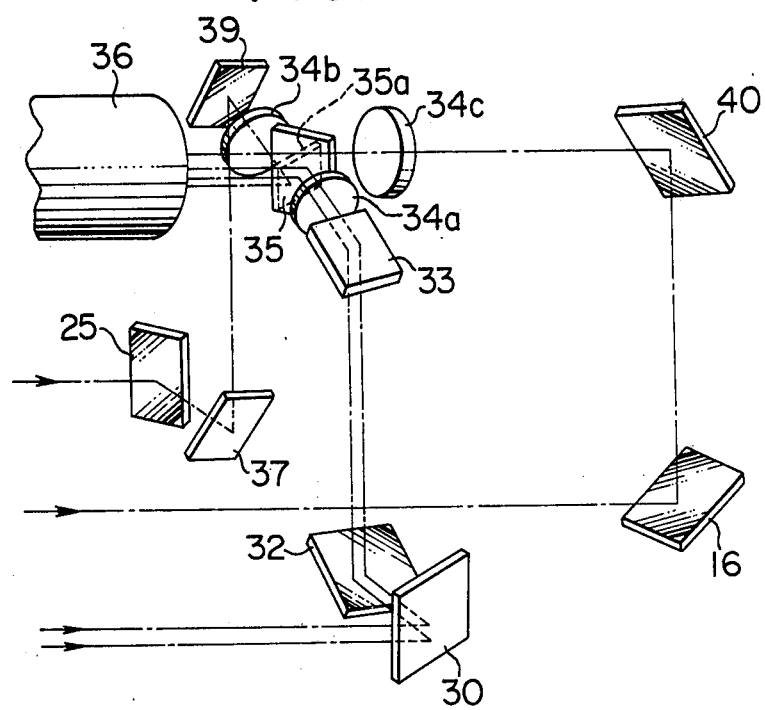
FIG. 2 is a perspective view showing the arrangement of optical elements for directing light bundles to a single image pick-up tube.
Figure 3:
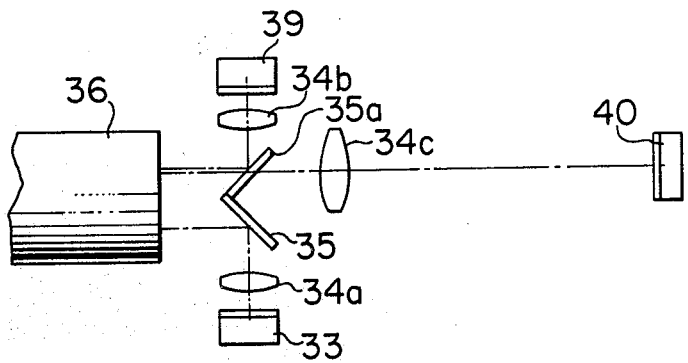
FIG. 3 is a plan view of the arrangement shown in FIG. 2.

Referring to FIGS. 2 and 3, it will be noted that the scale projecting light bundles which have been reflected by the mirror 30 are reflected upwardly by a further reflecting mirror 32, then laterally by a mirror 33, thereafter passed through a focusing lens 34a and reflected by a mirror 35 to pass to a photoelectric surface on an image pick-up tube 36.

It should further be noted that the sighting light bundle which has been reflected by the mirror 25 is again reflected upwardly by a reflecting mirror 37 and then laterally by a reflecting mirror 39. Thereafter, the light bundle is passed through a focusing lens 34b and reflected by a mirror 35a to be passed to the image pick-up tube 36.

The observing light bundle which has been reflected upwardly by the mirror 16 is then reflected by a mirror 40 and thereafter passed through a focusing lens 34c to the image pick-up tube 36. The mirror 35a is smaller in height than the mirror 35 so that the light boundle through the focusing lens 34c passed through a space above the mirror 35a.

In the projecting optical system, the projection of the target is made by using an infrared ray, preferably those portions of infrared ray having wave lengths close to those of visible light, so that infrared rays are passed through the observing and sighting optical systems. To the contrary, a visible light is used to project the scales. Therefore, the image pick-up tube as used herein has a sensibility both to the infrared ray and the visible light.

Figure 9:
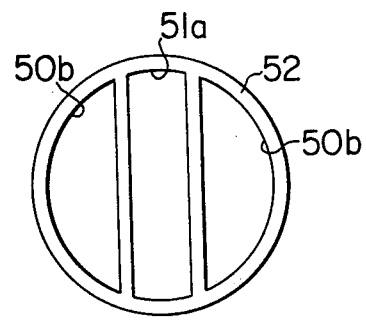
FIG. 9 shows an example of the aperture arrangement in accordance with the present invention.

Referring further to FIGS. 1 through 5, the target projecting optical system is provided with an aperture disc 50. Further, the observing optical system is provided with a slotted disc 51. These discs 50 and 51 are located in conjugate with the pupil of the patient's eye 13 with respect to the objective lens 12. The disc 50 is formed with a pair of substantially semicircular apertures 50b which are located with their chord portions opposed to each other with a space 50a provided therebetween. The disc 51 has a slot 51a located at a position corresponding to the space 50a of the disc 50. As shown in FIG. 9, the apertures 50b and the slot 51a are located within a circle 52 corresponding to the pupil of the patient's eye 13 so that they do not overlap with each other. According to the arrangement, the apertures 50b and the slot 51a are formed so that the patient's pupil is fully utilized to pass the light bundles so that any problem of lack of light energy can be solved.

Figure 6:
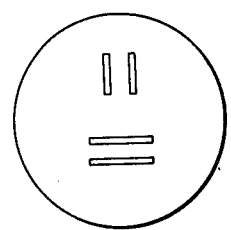
FIGS. 6 and 7 show examples of projected target image.
Figure 7:
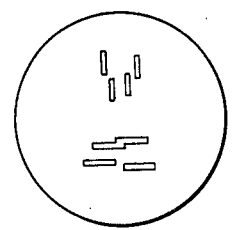

The target image produced by the projecting optical system on the retina will be correctly focused as shown in FIG. 6 when the patient's eye has a normal refractive power. However, in case where the patient's eye 13 is of near or far-sighted one, the target image will be split as for example shown in FIG. 7. In this instance, the target 6 is moved along the projecting optical aixs 5 until a correctly focused image is produced. The position of the target 6 along the axis 5 is designated on the scale 27 in terms of the corrective dioptral value and the value is projected on the image pick-up tube through the scale projecting system. For inspecting the astigmatism, the target image is observed while the image rotating device 14 is being rotated to find out the orientation of the astigmatic axes. The astigmatic axes are then designated in terms of an angle.

Figure 8:
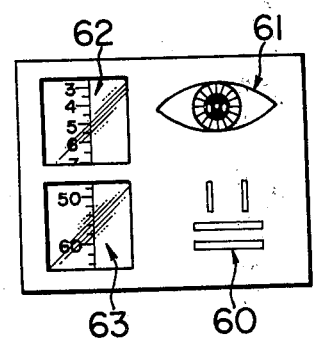
FIG. 8 shows an example of video display.

Referring to FIG. 8, there is shown an example of images displayed on a video tube in accordance with the inputs of the image pick-up tube 36. The target image as obtained through the observing system is shown by the reference numeral 60, the image of the anterior segment of the eye as obtained through the sighting system by 61, the dioptral value of the scale system by 62 and the angle of the astigmatic axis by 63.

Where the image pick-up tube is provided with means for maintaining the total intensity of photoelectric current constant throughout the photoelectric surface thereof, there is a tendency that the gain of the photoelectric surface is decreased due to a large value of the photoelectric current derived by the scale projection. As the result, the intensity of the light through the observing system becomes inadequate to produce a visible target image. In order to avoid the problem, the brightness of the background of the scale projecting system may be decreased. For example, the scales may have a dark background and transparent scale indentations.

In order to obtain an exact measurement, it is required to maintain the patient's eye in a condition seeing his far point. For the purpose, the refractmeter is provided with a viewing mark projecting system which comprises a collimater lens 42 for directing the light from the light source 1 along an optical axis 41 in the form of a parallel light bundle and a viewing mark plate 43 disposed on the optical axis 41. The light bundle through the mark plate 43 is passed through a lens 44, pentagonal prisms 45 and 46 and reflected by a mirror 47 and then through lenses 48 and 49 and the objective lens 12 to the patient's eye 13. Therefore, the measurement is performed by letting the patient's eye observe the projected mark.

Figure 10:
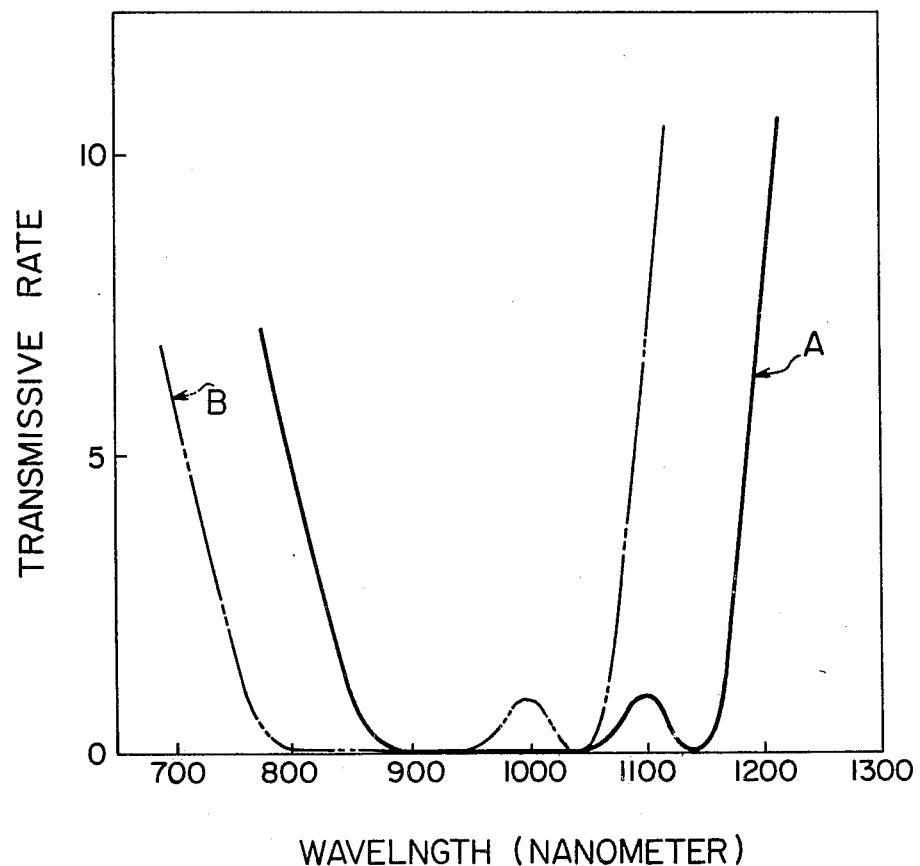
FIG. 10 shows the effect of the multiple layer coating on the image rotating element.

The image rotator 14 is coated at its reflecting surfaces with multiple layers of materials which are effective to increase the reflecting rate of the surfaces. Such coating is comprised of alternating layers of $ZrO_2$, $SiO_2$ and $TiO_2$, the thickness of each layer being approximately one-fourth of the wavelength of the light to be reflected. FIG. 10 shows the light transmissive rate of the coating having twenty-seven layers of such materials. In FIG. 10, the solid line A designate the transmissive rate with the incident angle of 0°, where the broken line B designates the one with the incident angle of 45°.

The invention has thus been shown and described with reference to specific embodiments, however, it should be noted that the invention is in no way limited to the details of the illustrated arrangements but changes and modifications may be made without departing from the scope of the appended claims.

We claim:

1. Eye refractmeter comprising a target projecting optical system including objective lens means for projecting an image of target means through the pupil of a patient's eye to produce a target image on retina of the eye, an observing optical system for observing the target image through the pupil and the objective lens means, and a sighting optical system for observing light reflected at an anterior segment of the eye to determine that the objective lens means is appropriately apart from the patient's eye, means being provided in said projecting optical system so that the image of the target means is projected by an infrared ray, said target projecting optical system including means for directing at least two target projecting light bundles through said pupil in different angles, said target projecting optical system further including aperture means located substantially in conjugate with the pupil with respect to the objective lens means, said aperture means including within a circle corresponding to the pupil a pair of substantially semicircular apertures located with their chord portions opposed to each other with a space therebetween, said observing optical system including second aperture means located substantially in conjugate with the pupil with respect to the objective lens means, said second aperture means including a slot located in a position corresponding to the space between said semicircular apertures.

2. Eye refractmeter in accordance with claim 1 which further includes surface reflector type image rotating means provided in one of the target projecting optical system and the observing optical system, said image rotating means having at least one reflecting surface formed with a coating of such materials which increase reflecting rate of the surface.

3. Eye refractmeter in accordance with claim 2 in which said coating comprises alternating layers of $ZrO_2$, $SiO_2$ and $TiO_2$.

4. Eye refractmeter in accordance with claim 2 in which said target projecting optical system and the observing optical system have a common optical path through the objective lens means and said image rotating means is provided in said common optical path.

* * * * *